(12) United States Patent
Carlson et al.

(10) Patent No.: US 8,020,427 B2
(45) Date of Patent: Sep. 20, 2011

(54) METHODS AND APPARATUS FOR INSITU ANALYSIS OF GASES IN ELECTRONIC DEVICE FABRICATION SYSTEMS

(75) Inventors: David K. Carlson, San Jose, CA (US); Satheesh Kuppurao, San Jose, CA (US)

(73) Assignee: Applied Materials, Inc., Santa Clara, CA (US)

(*) Notice: Subject to any disclaimer, the term of this patent is extended or adjusted under 35 U.S.C. 154(b) by 0 days.

(21) Appl. No.: 12/833,936

(22) Filed: Jul. 9, 2010

(65) Prior Publication Data
US 2010/0275674 A1 Nov. 4, 2010

Related U.S. Application Data

(62) Division of application No. 11/830,832, filed on Jul. 30, 2007, now Pat. No. 7,770,431.

(60) Provisional application No. 60/820,958, filed on Jul. 31, 2006.

(51) Int. Cl.
*G01N 7/00* (2006.01)
(52) U.S. Cl. .................................................. 73/23.21
(58) Field of Classification Search .................. 73/23.21
See application file for complete search history.

(56) References Cited

U.S. PATENT DOCUMENTS

| | | | |
|---|---|---|---|
| 3,930,756 A | 1/1976 | Bruggeman | |
| 4,112,736 A | 9/1978 | Wheldon et al. | |
| 4,633,083 A | 12/1986 | Knorr et al. | |
| 5,365,771 A | 11/1994 | Gysi et al. | |
| 5,552,600 A | 9/1996 | Davies et al. | |
| 6,040,915 A | 3/2000 | Wu et al. | |
| 6,076,392 A | 6/2000 | Drzewiecki | |
| 6,850,847 B2 | 2/2005 | Morrow et al. | |
| 7,770,431 B2 | 8/2010 | Carlson et al. | |
| 2004/0035183 A1 | 2/2004 | O'Brien et al. | |
| 2005/0082482 A1 | 4/2005 | Ludviksson | |

OTHER PUBLICATIONS

IPRP of International Application No. PCT/US2007/017038 dated Feb. 12, 2009.
International Search Report and Written Opinion of International Application No. PCT/US2007/017038 dated Dec. 18, 2007.
Office Action of U.S. Appl. No. 11/830,832 Mailed Oct. 9, 2008.
Jan. 9, 2009 Response to Office Action of U.S. Appl. No. 11/830,832 Mailed Oct. 9, 2008.
Final Office Action of U.S. Appl. No. 11/830,832 Mailed Mar. 4, 2009.
May 1, 2009 Response to Final Office Action of U.S. Appl. No. 11/830,832 Mailed Mar. 4, 2009.
Advisory Action of U.S. Appl. No. 11/830,832 Mailed May 12, 2009.
Supplemental Amendment of U.S. Appl. No. 11/830,832, filed Jun. 3, 2009.
Advisory Action of U.S. Appl. No. 11/830,832 Mailed Sep. 4, 2009.
Office Action of U.S. Appl. No. 11/830,832 Mailed Oct. 9, 2009.
Jan. 6, 2010 Response to Office Action of U.S. Appl. No. 11/830,832 Mailed Oct. 9, 2009.

(Continued)

*Primary Examiner* — Robert Raevis
(74) *Attorney, Agent, or Firm* — Dugan & Dugan, PC

(57) ABSTRACT

Systems and methods are disclosed that include adjusting a pressure level of a sample gas in a testing chamber, for example, using a pressurized inert reference gas, and determining a composition of the adjusted sample gas. By adjusting the pressure level of the sample gas, the composition of the sample gas may be determined more accurately than otherwise possible. Numerous other aspects are disclosed.

13 Claims, 8 Drawing Sheets

OTHER PUBLICATIONS

Final Office Action of U.S. Appl. No. 11/830,832 Mailed Jan. 20, 2010.
Mar. 22, 2010 Response to Final Office Action of U.S. Appl. No. 11/830,832 Mailed Jan. 20, 2010.
Notice of Allowance of U.S. Appl. No. 11/830,832 Mailed Apr. 2, 2010.
Restriction Requirement of U.S. Appl. No. 11/830,832 Mailed Mar. 17, 2008.
Jun. 17, 2008 Response to Restriction Requirement of U.S. Appl. No. 11/830,832 Mailed Mar. 17, 2008.
Examiner Interview Summary of U.S. Appl. No. 11/830,832 Mailed Dec. 4, 2008.
Examiner Interview Summary of U.S. Appl. No. 11/830,832 Mailed May 22, 2009.
Interview Summary of U.S. Appl. No. 11/830,832, filed Jun. 3, 2009.
Examiner Interview Summary of U.S. Appl. No. 11/830,832 Mailed Oct. 30, 2009.
Interview Summary of U.S. Appl. No. 11/830,832, filed Jan. 6, 2010.
Interview Summary of U.S. Appl. No. 11/830,832, filed Apr. 6, 2010.
Supplemental Notice of Allowance of U.S. Appl. No. 11/830,832 Mailed Apr. 7, 2010.

METHODS AND APPARATUS FOR INSITU ANALYSIS OF GASES IN ELECTRONIC DEVICE FABRICATION SYSTEMS

This application is a division of, and claims priority to, U.S. Non-Provisional patent application Ser. No. 11/830,832, filed Jul. 30, 2007, and titled, "METHODS AND APPARATUS FOR INSITU ANALYSIS OF GASES IN ELECTRONIC DEVICE FABRICATION SYSTEMS", which claims priority to U.S. Provisional Patent Application Ser. No. 60/820, 958 filed Jul. 31, 2006, and entitled "METHODS AND APPARATUS FOR INSITU ANALYSIS OF GASES IN ELECTRONIC DEVICE FABRICATION SYSTEM". Both of these patent applications are hereby incorporated by reference herein in their entirety for all purposes.

FIELD OF THE INVENTION

The present invention relates generally to electronic device fabrication methods and systems, and is more particularly concerned with insitu spectrographic analysis of gases in such systems.

BACKGROUND OF THE INVENTION

Electronic device fabrication methods and systems typically involve the use of various process gases and the creation of a number of by-products. In order to understand the processes better and to monitor the processes more closely, a sample of the process gases may be taken. However, such a sample may only reveal limited information about an overall process. Thus, what is needed are methods and apparatus that provide more complete and detailed information about process gases.

SUMMARY OF THE INVENTION

In some aspects of the invention, a method is provided that includes adjusting a pressure level of a sample gas; and determining a composition of the adjusted sample gas.

In other aspects of the invention, an apparatus for testing a sample gas is provided that includes a chamber adapted to contain a gas to be tested; a fitting coupled to the chamber and adapted to deliver a sample gas to the chamber; and a controller adapted to adjust a pressure level of the sample gas in the chamber.

In yet other aspects of the invention, a system for testing a sample gas is provided that includes a processing tool having a plurality of isolatable spaces containing gases to be tested; a chamber adapted to contain a sample gas to be tested; a fitting for selectively coupling the chamber to the plurality of spaces; and a controller adapted to adjust a pressure level of the sample gas in the chamber.

Other features and aspects of the present invention will become more fully apparent from the following detailed description of exemplary embodiments, the appended claims and the accompanying drawings.

DETAILED DESCRIPTION

The present invention provides systems and methods for performing analysis (e.g., infra read (IR) spectroscopy) on gases used or created in electronic device fabrication methods and systems. The methods and apparatus of the present invention facilitate analysis of gas samples taken from several locations within an electronic device fabrication system. Further the present invention provides methods of integrating one or more gas composition measurement devices into an electronic device fabrication system. For example, according to some embodiments of the present invention, an IR spectrophotometer may be coupled to a number of chambers and loadlocks of an electronic device fabrication system via a low pressure manifold that is operative to separately direct the flow of various gas samples to a sample cell of the IR spectrophotometer. Because IR spectroscopy may only be accurate at higher pressures (e.g., >100 Torr) and the process gases may be at lower pressures (e.g., <100 Torr) within the sample sites, the present invention further provides methods and apparatus to pressurize the sample gases to within a suitable range and in a controlled manner so that the composition and concentrations of the constituent parts of the sampled gases may be accurately determined.

The present invention may be useful for a number of different purposes. During the manufacture of an electronic device (e.g., a semiconductor device), various processes are performed which may contaminate spaces (e.g., process chamber, transfer chamber, load lock, factory interface, clean room, etc.) in which processing is conducted or through which manufactured articles are passed. For example, deposition species, deposition by-products, etchant, process gases, etc., may contaminate the spaces. Accordingly, in some embodiments, the present invention may be employed to determine a contamination level within a space. Further, if a process does not work as expected, the present invention may be employed to help determine what actually happened during the process so that the process may be corrected or improved. In addition, many waste abatement processes (e.g., methods of processing or neutralizing toxic by-products) may be improved or optimized with more accurate information regarding the composition of the waste gases. Thus, the present invention may be employed to determine the composition of the waste gases to improve abatement processes. The present invention may have many other applications than the examples listed above.

Figure 1:
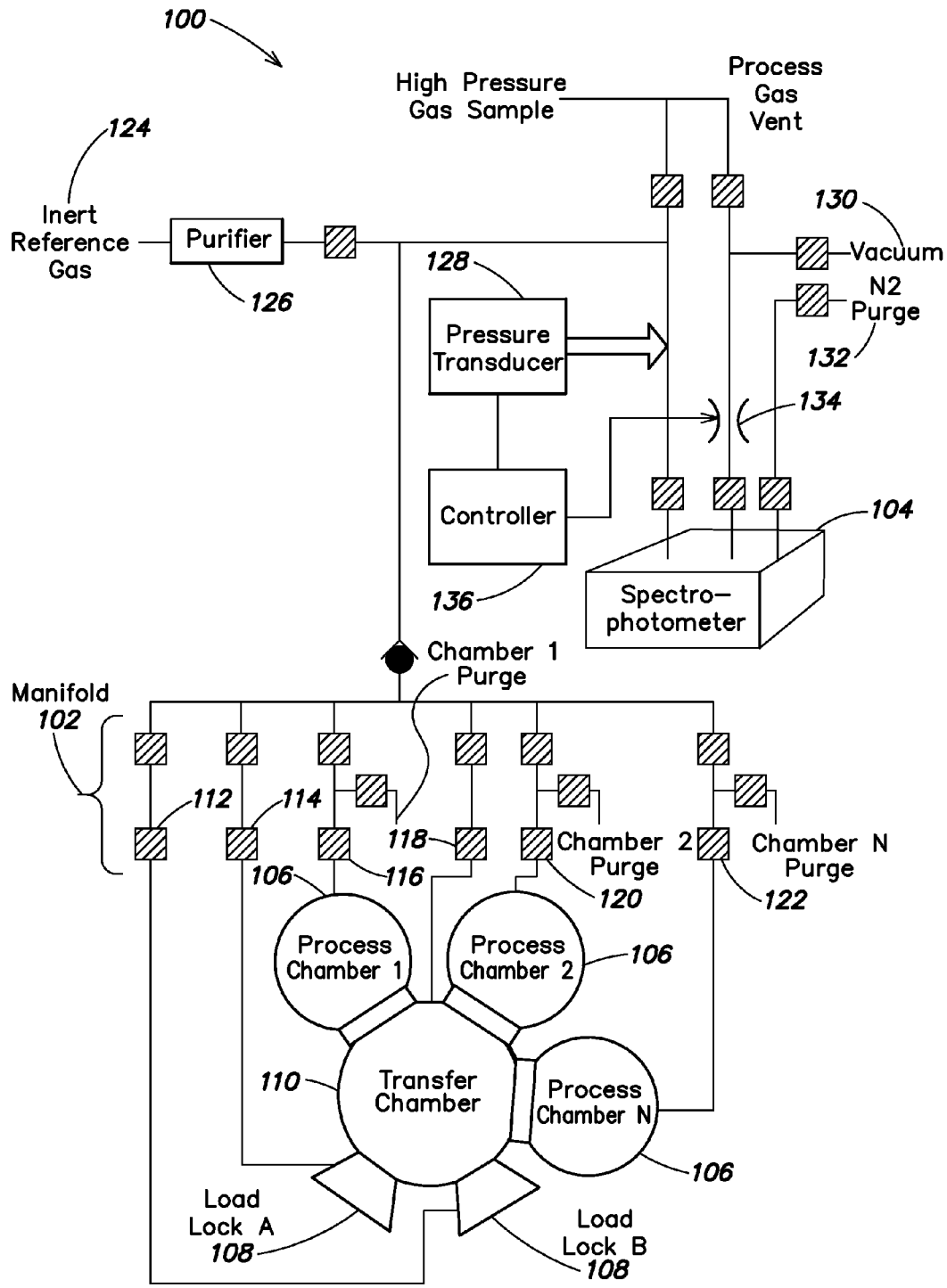
FIG. 1 is a schematic block diagram depicting an example embodiment according to some aspects of the present invention.

Turning to FIG. 1, a schematic view of a system 100 which may be used to analyze a sample gas (e.g., exhaust gas) from a space (e.g., process chamber, load lock, transfer chamber, etc.) in accordance with an exemplary embodiment of the present invention is depicted. In some embodiments of the present invention, the sample gas may be analyzed to determine a contamination level within the space. The system 100 may include a fitting 102 (e.g., a low pressure manifold which may include a plurality of normally closed valves and a one way check valve) operative to selectively, fluidly couple a sample cell within a measurement device 104 (e.g., an IR spectrophotometer) to various spaces such as, for example, one or more process chambers 106, one or more load locks 108, one or more transfer chambers 110 (only one shown), or the like. Each of the spaces may include an associated port (e.g., a valve) 112 to 122 as part of the fitting 102. In some embodiments of the present invention, the fitting 102 may be selectively, fluidly coupled with any number of spaces. The system 100 may also include a supply 124 (e.g., inert reference gas such as $N_2$) and a purifier 126 in fluid communication with the sample cell of the measurement device 104. The system 100 may also include a pressure monitoring device 128 (e.g., a transducer), a vacuum source 130, a purge supply 132, and an adjustable orifice 134 (e.g., a variable flow valve) operatively coupled with an outlet of the sample cell of the measurement device 104.

The various components may each be operatively coupled to (e.g., electrically) and operated under the control of a controller 136. Although these couplings are not depicted for clarity, the connection between the controller 136 and the pressure monitoring device 128; and the controller and the adjustable orifice 134 are shown. As will be explained in more detail below, the pressure monitoring device 128 is operative to provide (e.g., feedback) gas pressure information within the sample cell of the measurement device 104 to the controller 136. The controller is operative to adjust the adjustable orifice 134 to control the pressure within the sample cell of the measurement device 104.

Figure 2:
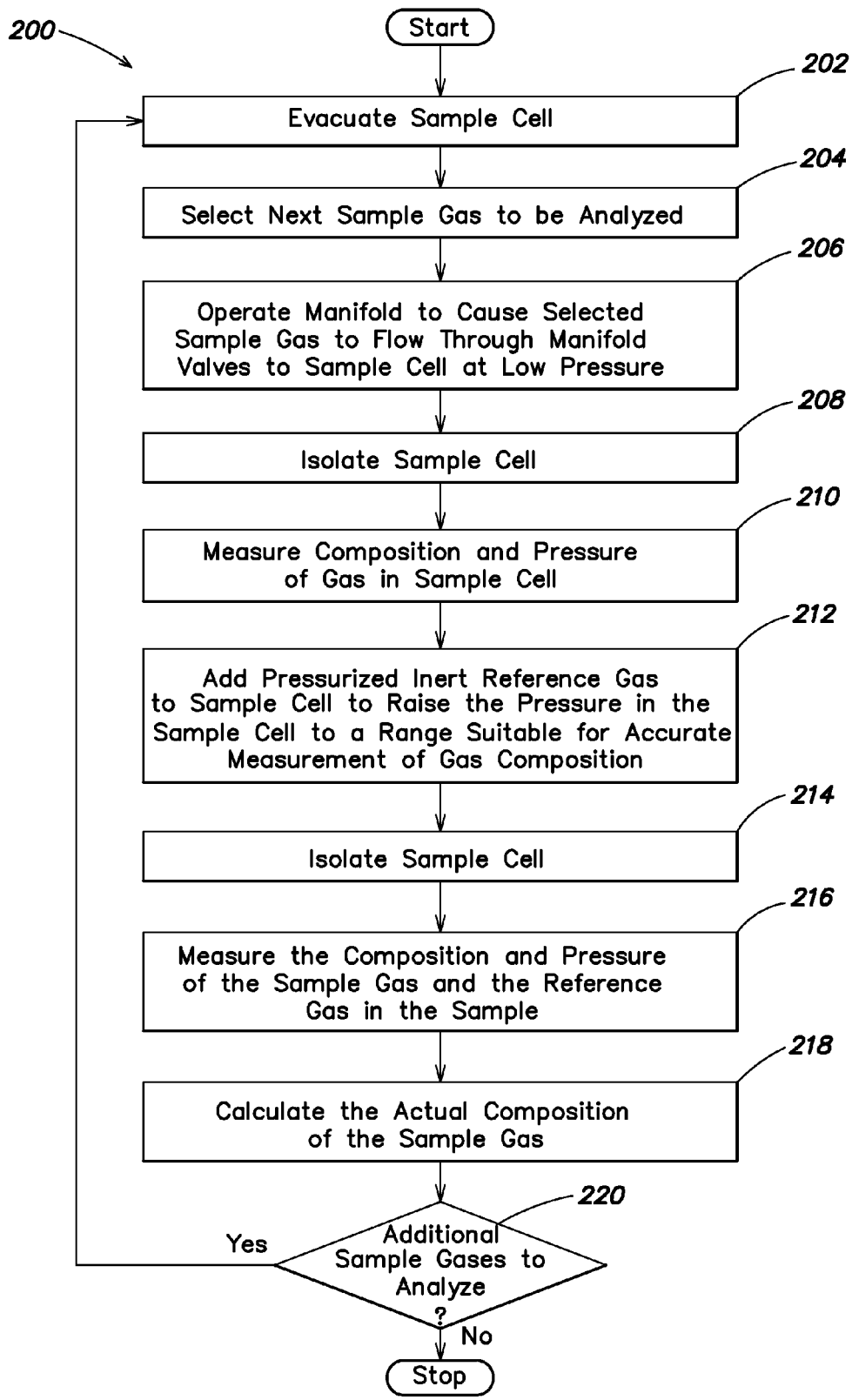
FIG. 2 is a flowchart depicting an example method embodiment associated with the example apparatus of FIG. 1 according to some aspects of the present invention.

Turning to FIG. 2, an example method 200 of the present invention is depicted. In step 202, the sample cell of the measurement device 104 may be evacuated by selectively coupling (e.g., opening a valve) the vacuum source 130 to the sample cell of the measurement device 104. In some embodiments, the sample cell of the measurement device 104 may be purged with inert gas (e.g., $N_2$) before the evacuation step. In other words, the sample cell of the measurement device 104 may be purged by selectively coupling (e.g., opening a valve) the purge supply 132 to the sample cell of the measurement device 104 before the evacuation step 202. In step 204, the controller may select a space 106, 108, 110 from which to sample gas. In step 206, the fitting 102 may be operated to cause the selected gas to flow to the sample cell of the measurement device 104. The selected sample gas may flow on its own at a low pressure (e.g., <100 Torr) and/or the selected sample gas may be drawn by the vacuum source 130. Once the sample cell is filled with the selected sample gas at the low pressure level indicated by the pressure monitoring device 128, the sample cell may be isolated in step 208 by closing off the inlet and outlet valves of the sample cell. In step 210, the composition and pressure of the gas in the sample cell may be measured and recorded.

In step 212, pressurized inert reference gas from the supply 124 is added to the sample cell to raise the pressure in the sample cell to a range suitable for accurate measurement of gas composition, for example, using an IR spectrophotometer. The variable orifice 134, under the control of the controller 136, is used to control the pressure within the sample cell. Once the desired pressure range (e.g., >100 Torr) is achieved as indicated to the controller 136 by the pressure monitor 128, in step 214, the sample cell is again isolated (e.g., the inlet and outlet valves are closed). In step 216, the composition and pressure of the combination of the sample gas and the reference gas in the sample cell is measured. In step 218, the actual composition of the sample gas is calculated based upon the measured values determined in steps 210 and 216 (e.g., the composition of the sample gas alone is determined by adjusting for the added reference gas). In step 220, the controller 136 determines if there are additional sample gases to analyze. If there are, control flows back to step 202 where the method 200 is repeated for the remaining sample gases. If sample gas from each of spaces 106, 108, 110 has been analyzed, the method 200 ends after step 220.

Figure 3:
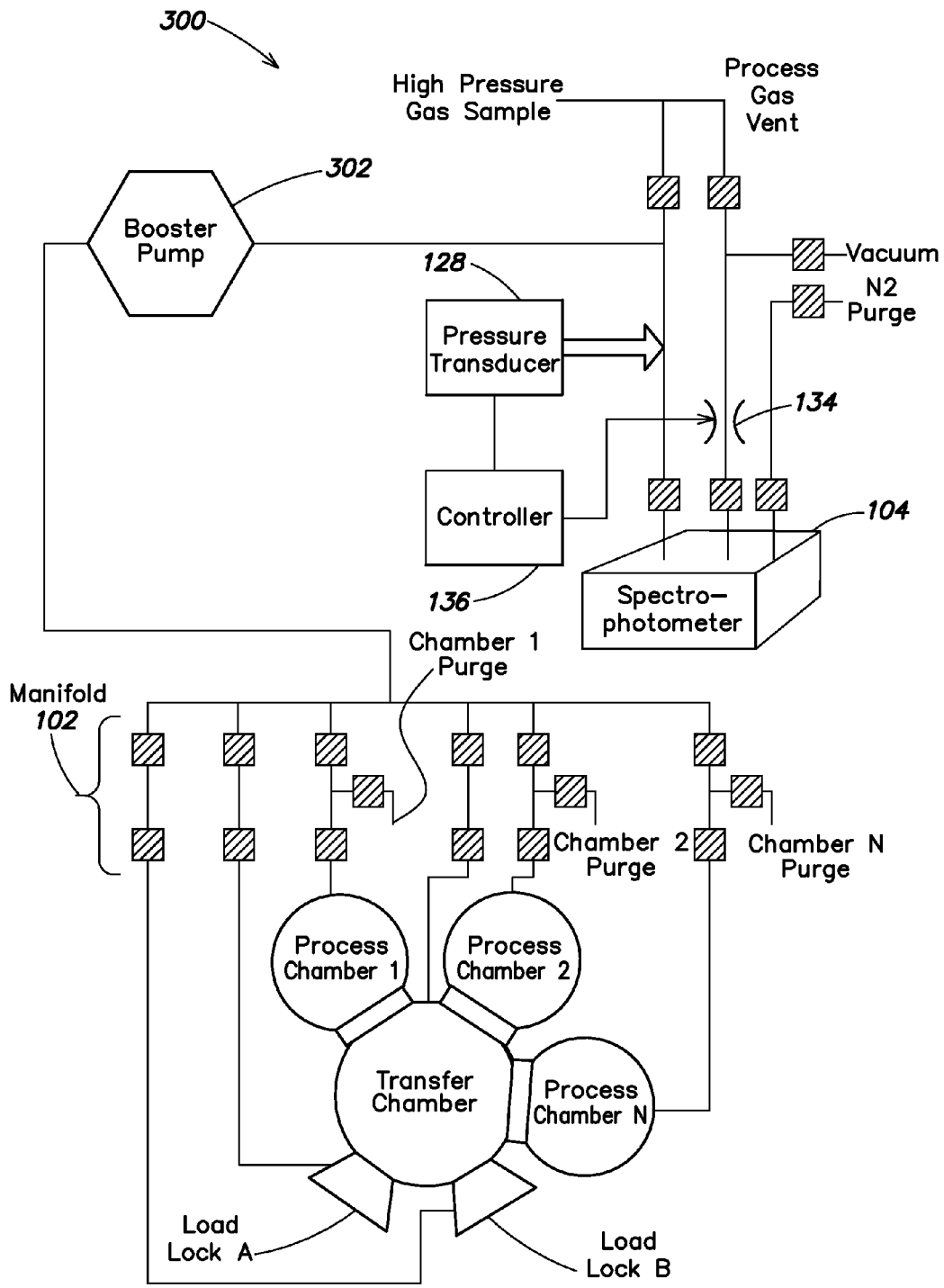
FIG. 3 is a schematic block diagram depicting a second example embodiment according to some aspects of the present invention.
Figure 4A:
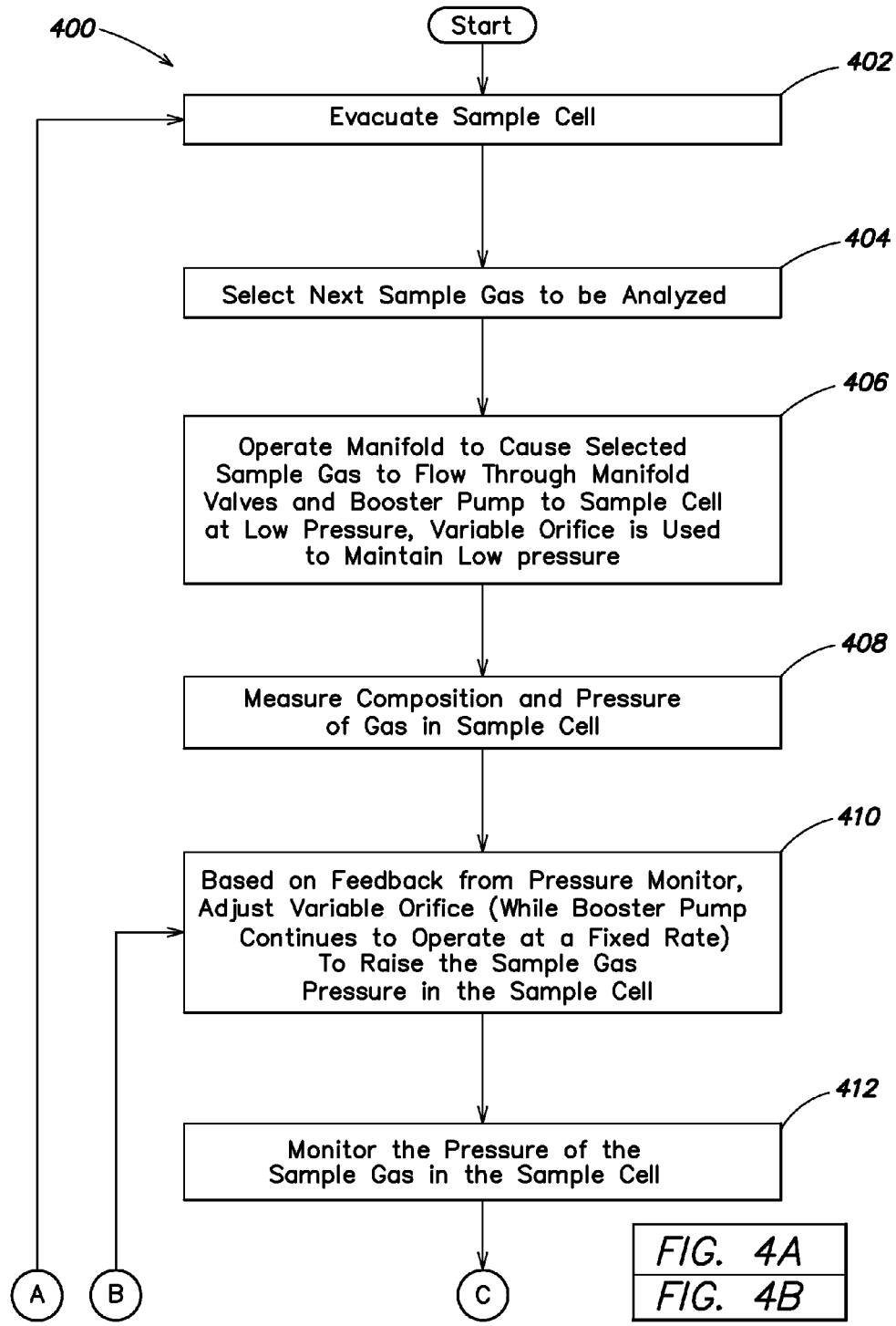
FIGS. 4A and 4B together are a flowchart depicting an example method embodiment associated with the example apparatus of FIG. 3 according to some aspects of the present invention.
Figure 4B:
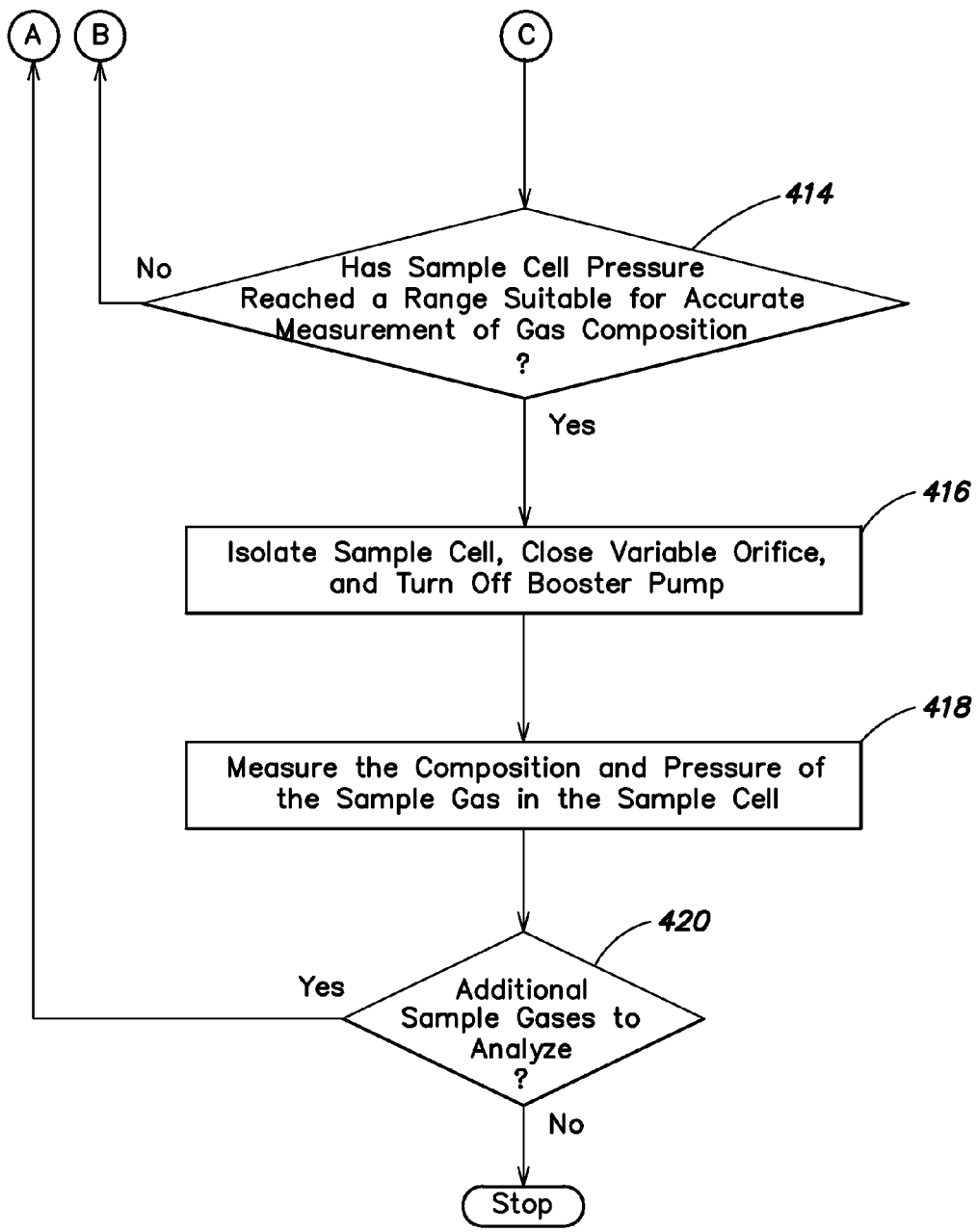

Turning to FIGS. 3, 4A, and 4B, an alternative embodiment of a system 300 and method 400 according to some embodiments of the present invention is depicted. In the system 300 of FIG. 3, a booster pump 302 coupled between the fitting 102 and the sample cell of the measurement device 104 is used to pressurize the selected sample gas (e.g., instead of the pressurized reference inert gas supply used in the system 100 depicted in FIG. 1). As with the embodiment of FIG. 1, the variable orifice 134, under the control of the controller 136, is used to control the pressure within the sample cell. Once the desired pressure range (e.g., >100 Torr) is achieved as indicated to the controller 136 by the pressure monitor 128, the sample cell is isolated (e.g., the inlet and outlet valves are closed). Thus in the method 400 and system 300 of FIGS. 4 and 3, respectively, feedback from the pressure monitor 128 is used to control the variable orifice 134.

In step 402 of the example method 400, a sample cell (e.g., a sample chamber of spectrophotometer 104) is evacuated. In step 404, a controller 136 (or user) selects a next space whose gas is to be tested. In step 406, a manifold (e.g., fitting 102 (FIG. 3)) is used to flow the sample gas from the selected space through the booster pump 302 to the sample cell. A variable orifice 134 is used to maintain low pressure (e.g., a pressure related or equal to the pressure in the space to be tested). In step 408, the composition and pressure of the sample gas is measured in the sample cell. In step 410, based on feedback from a pressure monitor, the variable orifice is adjusted (while the booster pump continues to operate at a fixed rate) to adjust (e.g., increase) the sample gas pressure in the sample chamber. In step 412, the pressure in the sample chamber is monitored. In step 414, a determination is made whether the pressure has reached a level suitable for accurate determination of the sample gas composition. If it has not, flow proceeds back to step 410. If it has, in step 416, the sample cell is isolated (e.g., the inlet and outlet (e.g., variable orifice) are closed) and the booster pump is shut down. In step 418, the composition and pressure of the sample gas is again measured in the sample cell. In step 420, a determination is made whether there are additional spaces with gas to be analyzed. If so, flow returns to step 402. Otherwise the method 400 ends.

Figure 5:
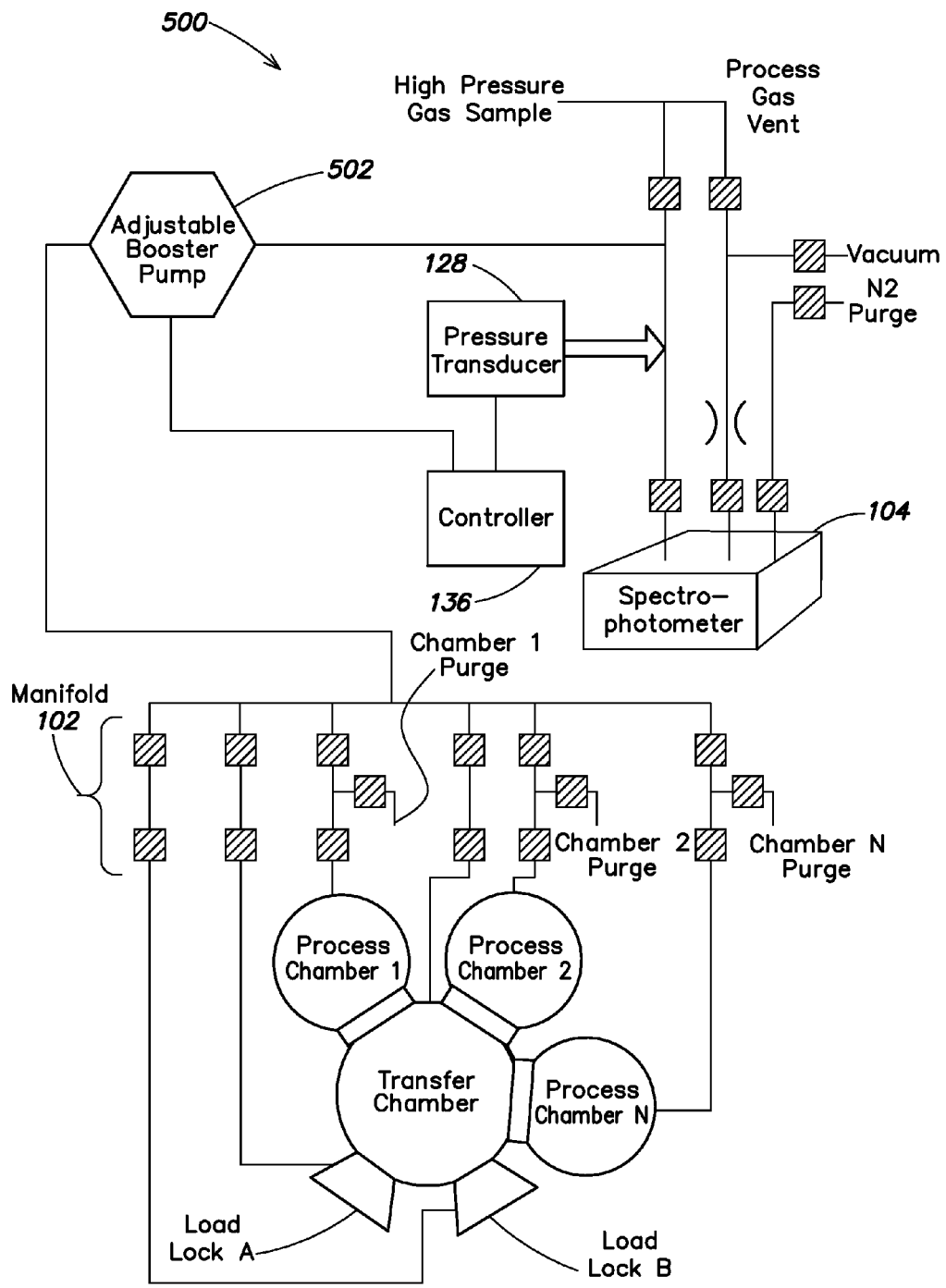
FIG. 5 is a schematic block diagram depicting a third example embodiment according to some aspects of the present invention.
Figure 6A:
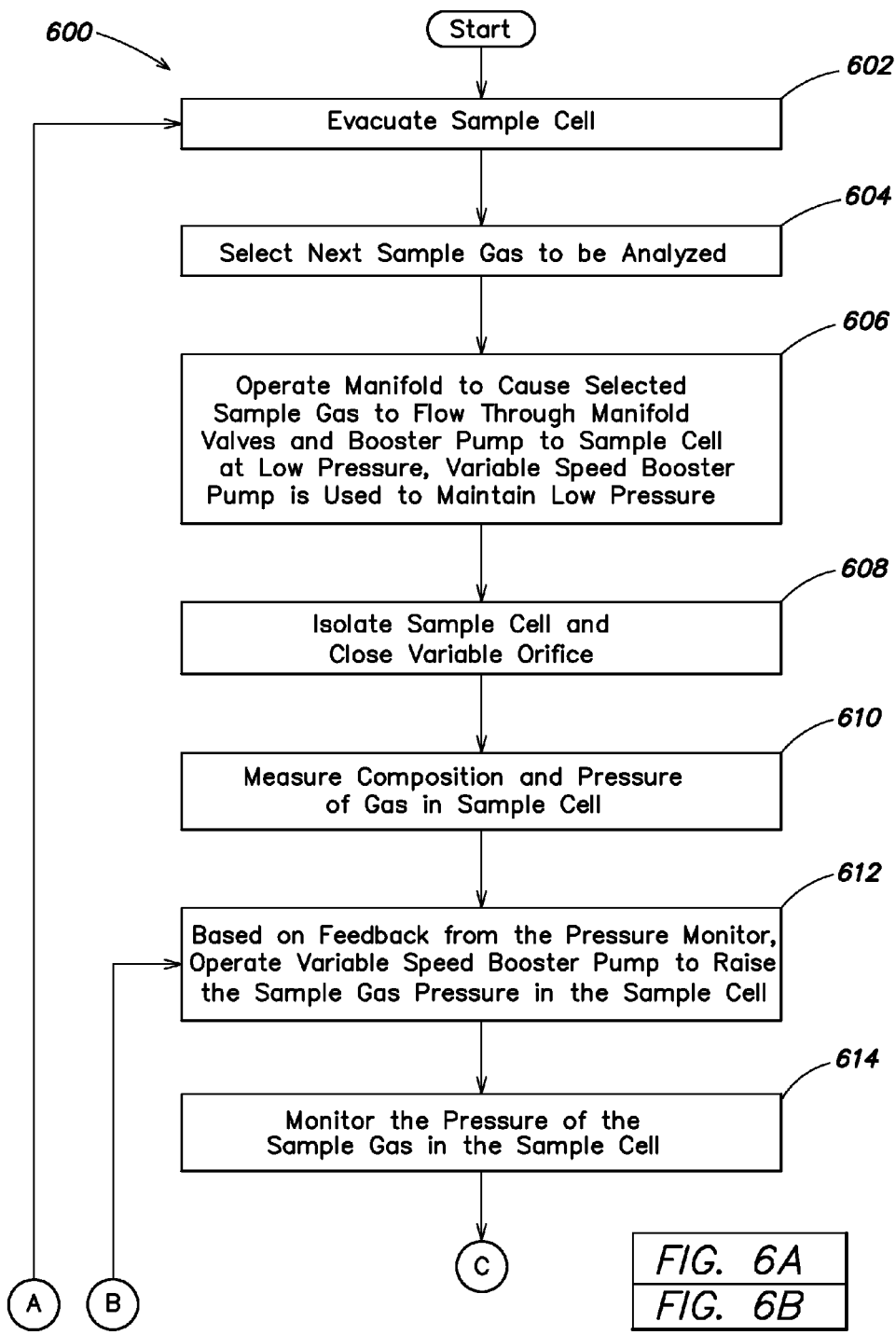
FIGS. 6A and 6B together are a flowchart depicting an example method embodiment associated with the example apparatus of FIG. 5 according to some aspects of the present invention.
Figure 6B:
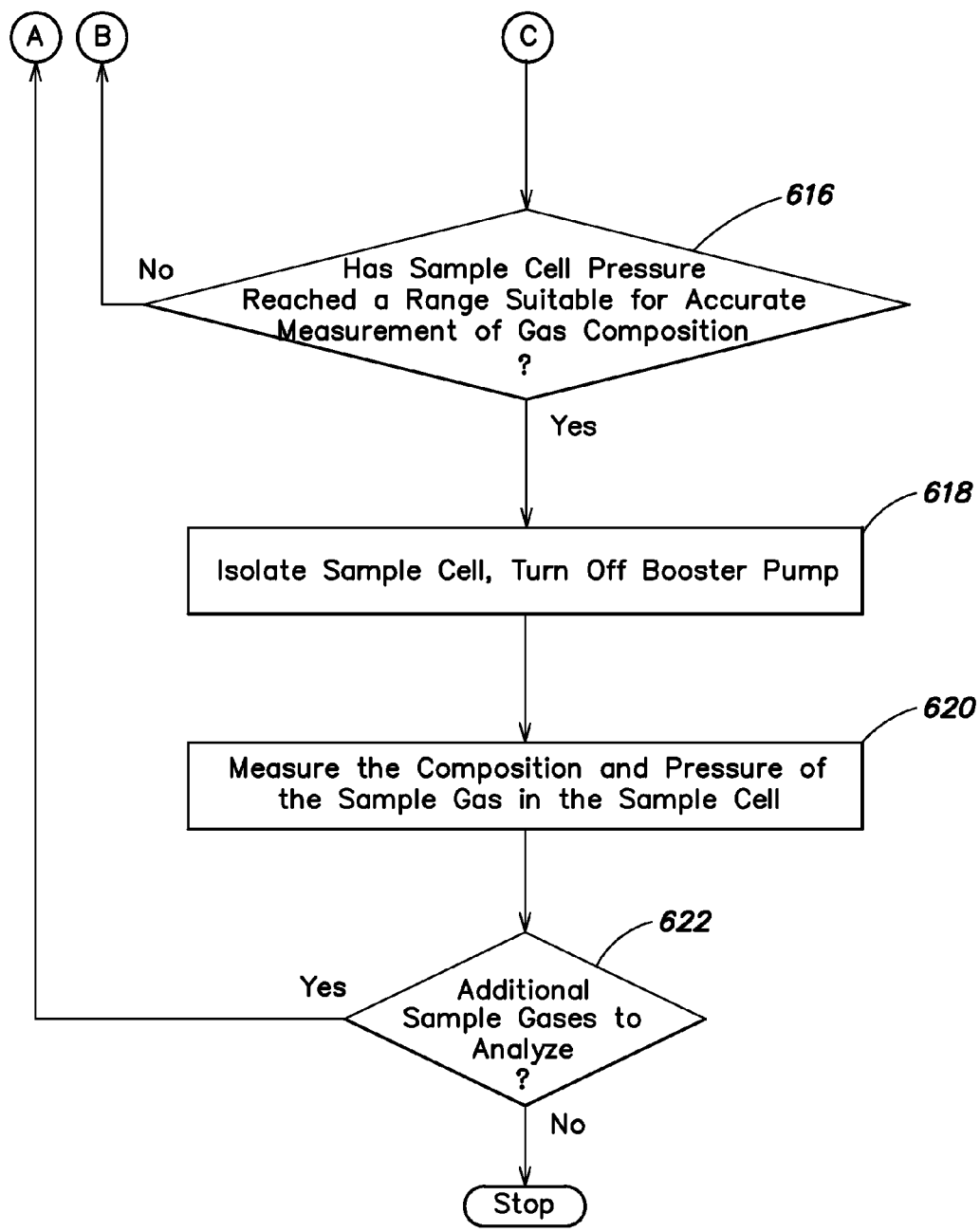

Turning to FIGS. 5, 6A, and 6B, an alternative embodiment of a system 500 and method 600 according to some embodiments of the present invention is depicted. In the system 500 of FIG. 5, an adjustable booster pump 502 coupled between the fitting 102 and the sample cell of the measurement device 104, is used to pressurize the selected sample gas (e.g., instead of the pressurized reference inert gas supply used in the system 100 depicted in FIG. 1 or the booster pump 302 and variable orifice 134 of the system 300 depicted in FIG. 3). The adjustable booster pump 502, under the control of the controller 136, is used to control the desired pressure within the sample cell. Once the desired pressure range (e.g., >100 Torr) is achieved as indicated to the controller 136 by the pressure monitor 128, the sample cell is isolated (e.g., the inlet and outlet valves are closed). Thus in the method 600 and system 500 of FIGS. 6A & 6B and 5, respectively, feedback from the pressure monitor 128 is used to control the adjustable booster pump 502.

In step 602 of the example method 600, a sample cell (e.g., a sample chamber of spectrophotometer 104) is evacuated. In step 604, a controller 136 (or user) selects a next space whose gas is to be tested. In step 606, a manifold (e.g., fitting 102 (FIG. 5)) is used to flow the sample gas from the selected space through a variable speed (e.g., adjustable) booster pump 502 to the sample cell. A variable speed (e.g., adjustable) booster pump 502 is used to maintain low pressure (e.g., a pressure related or equal to the pressure in the space to be tested). In step 608, the sample cell is isolated, for example, by closing the inlets and outlets. In step 610, the composition and pressure of the sample gas is measured in the sample cell. In step 612, based on feedback from a pressure monitor 128 for example, operation of the variable speed booster pump is adjusted to adjust (e.g., increase) the sample gas pressure in the sample chamber. In step 614, the pressure in the sample chamber is monitored. In step 616, a determination is made whether the pressure has reached a level suitable for accurate determination of the sample gas composition. If it has not, flow proceeds back to step 612. If it has, in step 618, the sample cell is isolated (e.g., the inlet and outlet are closed) and the booster pump is shut down. In step 620, the composition and pressure of the sample gas is again measured in the sample cell. In step 622, a determination is made whether there are additional spaces with gas to be analyzed. If so, flow returns to step 602. Otherwise the method 600 ends.

The foregoing description discloses only particular embodiments of the invention; modifications of the above disclosed methods and apparatus which fall within the scope of the invention will be readily apparent to those of ordinary skill in the art.

Accordingly, while the present invention has been disclosed in connection with specific embodiments thereof, it should be understood that other embodiments may fall within the spirit and scope of the invention, as defined by the following claims.

The invention claimed is:

1. A method for testing a sample gas comprising:
   adjusting a pressure level of a sample gas; and
   determining a composition of the adjusted sample gas;
   wherein the adjusting includes adjusting the pressure level from a low pressure at which measurement by spectroscopy would not be accurate to a higher pressure within a high enough suitable range at which the composition of the sample gas is capable of being accurately determined by spectroscopy; and
   wherein adjusting the pressure level includes:
      adding additional sample gas to the sample gas in an isolatable chamber; and
      controlling an adjustable booster pump supplying additional sample gas.

2. The method of claim 1 wherein controlling the adjustable booster pump further comprises:
   receiving feedback from a pressure monitor.

3. The method of claim 2 further comprising:
   adjusting operation of the adjustable booster pump based on the feedback.

4. The method of claim 1 further comprising:
   isolating the sample cell once a desired pressure range is achieved.

5. The method of claim 1 wherein determining a composition of the adjusted sample gas includes measuring a pressure of the sample gas before and after the pressure level of the sample gas is adjusted.

6. The method of claim 5 further comprising:
   determining whether the measured pressure has reached a level suitable for accurate determination of the sample gas composition.

7. An apparatus for testing a sample gas comprising:
   a chamber adapted to contain a gas to be tested;
   a fitting coupled to the chamber and adapted to deliver a sample gas to the chamber; and
   a controller adapted to adjust a pressure level of the sample gas in the chamber; wherein the adjustment includes adjusting the pressure level from a low pressure at which measurement by spectroscopy would not be accurate to a higher pressure within a high enough suitable range at which a composition of the sample gas is capable of being accurately determined by spectroscopy; and
   wherein the controller is coupled to a sample gas supply and adapted to adjust the pressure level by controlling an adjustable booster pump coupled to the controller to supply additional sample gas to the sample gas in the chamber.

8. The apparatus of claim 7 wherein the controller is coupled to a pressure monitor.

9. The apparatus of claim 8 wherein the pressure monitor is adapted to provide feedback to the controller regarding the pressure level.

10. A system for testing sample gases comprising:
    a processing tool having a plurality of isolatable spaces containing gases to be tested;
    a chamber adapted to contain a sample gas to be tested;
    a fitting for selectively coupling the chamber to the plurality of spaces; and
    a controller adapted to adjust a pressure level of the sample gas in the chamber; wherein the adjustment includes adjusting the pressure level from a low pressure at which measurement by spectroscopy would not be accurate to a higher pressure within a high enough suitable range at which a composition of the sample gas is capable of being accurately determined by spectroscopy; and
    wherein the controller is coupled to a sample gas supply.

11. The system of claim 10 wherein the controller is coupled to a booster pump.

12. The system of claim 10 wherein the controller is coupled to an adjustable booster pump.

13. The system of claim 10 wherein the controller is coupled to a pressure monitor; and
    wherein the pressure monitor is adapted to provide feedback to the controller regarding the pressure level.

* * * * *